(12) United States Patent
Rimboeck et al.

(10) Patent No.: US 11,691,884 B2
(45) Date of Patent: Jul. 4, 2023

(54) METHOD OF CLASSIFYING METALLURGICAL SILICON

(71) Applicant: WACKER CHEMIE AG, Munich (DE)

(72) Inventors: Karl-Heinz Rimboeck, Heldenstein (DE); Uwe Paetzold, Burghausen (DE); Gerhard Traunspurger, Waging am See (DE)

(73) Assignee: WACKER CHEMIE AG, Munich (DE)

( * ) Notice: Subject to any disclaimer, the term of this patent is extended or adjusted under 35 U.S.C. 154(b) by 338 days.

(21) Appl. No.: 16/603,662

(22) PCT Filed: Feb. 8, 2018

(86) PCT No.: PCT/EP2018/053210
§ 371 (c)(1),
(2) Date: Oct. 8, 2019

(87) PCT Pub. No.: WO2019/154502
PCT Pub. Date: Aug. 15, 2019

(65) Prior Publication Data
US 2021/0087066 A1    Mar. 25, 2021

(51) Int. Cl.
*C01B 33/107* (2006.01)
*G01N 33/2022* (2019.01)
*C01B 33/037* (2006.01)

(52) U.S. Cl.
CPC ...... *C01B 33/10742* (2013.01); *C01B 33/037* (2013.01); *G01N 33/2022* (2019.01); *C01P 2004/61* (2013.01); *C01P 2006/80* (2013.01)

(58) Field of Classification Search
CPC ............ C01B 33/10742; C01B 33/037; G01N 33/2022
See application file for complete search history.

(56) References Cited

U.S. PATENT DOCUMENTS 4,092,446 A    5/1978   Padovani et al.
4,877,596 A   10/1989   Schwirtlich et al.
(Continued)

FOREIGN PATENT DOCUMENTS

DE   102015210762 A1   12/2016
EP        0260424 B1    5/1990
(Continued)

OTHER PUBLICATIONS

K. Hesse, et al., "Survey over the TCS process", Silicon for the Chemical Industry VIII, Jun. 12-15, 2006, pp. 157-166, Silicon for the Chemical Industry VIII, Trondheim, Norway.
(Continued)

*Primary Examiner* — James A Fiorito
(74) *Attorney, Agent, or Firm* — Brooks Kushman P.C.

(57) ABSTRACT

Metallurgical silicon containing impurities of carbon and/or carbon-containing compounds is classified and subsequently used selectively for chlorosilane production. The process comprises the steps of:

a) determining the free carbon proportion which reacts with oxygen up to a temperature of 700° C., b) directing metallurgical silicon in which the free carbon proportion is ≤150 ppmw to a process for producing chlorosilanes and/or directing metallurgical silicon in which the free carbon proportion is >150 ppmw to a process for producing methylchlorosilanes.

As a result of the process, metallurgical silicon having a total carbon content of up to 2500 ppmw can be used for producing chlorosilanes.

20 Claims, 4 Drawing Sheets

(56) References Cited

U.S. PATENT DOCUMENTS

| | | | |
|---|---|---|---|
| 2007/0248521 A1* | 10/2007 | Kutsovsky | C01B 33/035 |
| | | | 423/324 |
| 2011/0229398 A1 | 9/2011 | Troll et al. | |
| 2014/0050648 A1 | 2/2014 | Becker et al. | |
| 2015/0110702 A1* | 4/2015 | Gupta | C01B 33/027 |
| | | | 423/350 |
| 2015/0170976 A1 | 6/2015 | Funazaki et al. | |
| 2016/0002052 A1* | 1/2016 | Ishida | C01B 33/1071 |
| | | | 423/342 |
| 2018/0008381 A1 | 1/2018 | Balkenhol et al. | |

FOREIGN PATENT DOCUMENTS

| | | | |
|---|---|---|---|
| EP | 2957543 B1 | 10/2018 | |
| JP | 2004149351 A | 5/2004 | |
| KR | 20120013071 A | 2/2012 | |
| KR | 20150032859 A | 3/2015 | |
| WO | 2010028878 A1 | 3/2010 | |
| WO | 2012109459 A1 | 8/2012 | |
| WO | 16198264 A1 | 12/2016 | |

OTHER PUBLICATIONS

H. Kohno et al., "Quality Requirements for Silicon Metal in Polysilicon Production", Silicon for the Chemical Industry II, Jun. 8-10, 1994, pp. 165-170, Silicon for the Chemical Industry II, Trondheim, Norway.

J.P. Svanem et al., "Analytical Method to Measure Different Forms of Carbon in Silicon", Silicon for the Chemical and Solar Industry XI, Jun. 25-29, 2012, pp. 145-156, Bergen-Ulvik, Norway.

* cited by examiner

METHOD OF CLASSIFYING METALLURGICAL SILICON

CROSS REFERENCE TO RELATED APPLICATIONS

This application is the U.S. National Phase of PCT Appln. No. PCT/EP2018/053210 filed Feb. 8, 2016, the disclosure of which is incorporated in its entirety by reference herein.

BACKGROUND OF THE INVENTION

1. Field of the Invention

The invention relates to a process for classification of metallurgical silicon containing impurities of carbon and/or carbon-containing compounds and to the use of metallurgical silicon having a total carbon content of up to 2500 ppmw for producing chlorosilanes.

2. Description of the Related Art

Metallurgical silicon ($Si_{mg}$, "metallurgical grade" silicon) or else "crude silicon" is produced on an industrial scale by reduction of silicon dioxide with carbon in an electric arc furnace at a temperature of about 2000° C. The purity of $Si_{mg}$ is typically about 98-99%.

$Si_{mg}$ is the starting material for the production of methylchlorosilanes by the Müller-Rochow process. Methylchlorosilanes are used in particular for producing silicones.

It is also used as a starting material in photovoltaics. To this end, the $Si_{mg}$ must be purified and converted into solar silicon ($Si_{sg}$, "solar grade" silicon), which generally comprises impurities of less than 0.01%. To achieve this it is for example reacted with gaseous hydrogen chloride at 300° C. to 700° C. in a fluidized bed reactor to afford chlorosilanes, in particular trichlorosilane (TCS, $HSiCl_3$). This is followed by distillation steps to further purify the chlorosilanes. The thus obtained chlorosilanes then serve as a starting material for the production of polycrystalline silicon (poly-Si).

Poly-Si may be produced in the form of rods by the Siemens process, wherein elemental silicon is deposited from the gas phase onto heated filament rods in a reactor.

The process gas employed is usually a mixture of TCS and hydrogen. Poly-Si may alternatively be produced in the form of a granulate. Here, silicon particles are fluidized and heated by means of a gas flow in a fluidized bed reactor. Addition of a silicon-containing reaction gas, for example TCS, results in deposition of elemental silicon onto the hot particle surfaces, thus causing the particles to grow in diameter.

Poly-Si is in turn a starting material in the production of multicrystalline $Si_{sg}$, for example by the ingot casting process. Solar cells can then be manufactured from the $Si_{sg}$.

The abovementioned conversion of $Si_{mg}$ into chlorosilanes, for example TCS, may be effected by two processes based on the following reaction equations (cf. WO2010/028878A1 and WO2016/198264A1):

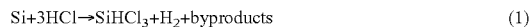
(1)

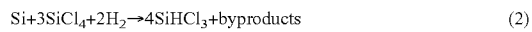
(2)

Byproducts that may be formed include further halosilanes, for example monochlorosilane($H_3SiCl$), dichlorosilane ($H_2SiCl_2$), silicon tetrachloride (STC, $SiCl_4$), and di- and oligosilanes. Impurities such as hydrocarbons, organochlorosilanes and metal chlorides may also be constituents of the byproducts. To form high-purity TCS, a distillation therefore follows.

In the hydrochlorination according to reaction (1) chlorosilanes may be produced from $Si_{mg}$ by addition of hydrogen chloride (HCl) in a fluidized bed reactor at 300° C. to 700° C., the reaction proceeding exothermically. This generally affords TCS and STC as primary products.

The low temperature conversion (LTC) according to reaction (2) is performed in the presence of a catalyst (for example Cu). The LTC may be carried out in a fluidized bed reactor in the presence of $Si_{mg}$ at temperatures between 400° C. and 700° C.

It is known that carbon or carbon-containing impurities in the production of poly-Si result in diminished quality (negative effects on the electrical properties) of the poly-Si itself and of the descendent products thereof. For example carbon-containing impurities may result in defects in the crystal lattice of silicon single crystals produced from poly-Si and/or in accelerated formation of oxygen precipitates.

It is therefore important to keep the carbon content as low as possible over the entire poly-Si production process.

The carbon-containing impurities may be introduced into the process for example from carbon-containing components of the Siemens or fluidized bed reactors. The reactants used in the production process, which can contain carbon or carbon-containing compounds as impurities, represent a further carbon source.

A primary cause for carbon-containing impurities are the reactants $Si_{mg}$, hydrogen and hydrogen chloride (HCl) used in the production of chlorosilanes. For example the reaction gases may contain methane, ethane, carbon monoxide and carbon dioxide ($CO_2$). These compounds may originate in particular from recovered hydrogen and/or HCl.

$Si_{mg}$ which is generally in particulate form and has a purity of 98% to 99% may contain the following elements in addition to carbon: Fe, Ca, Al, Ti, Cu, Mn, Cr, V, Ni, Co, W, Mo, As, Sb, Bi, S, Se, Te, Zr, Ge, Sn, Pb, Zn, Cd, Sr, Ba, Y, Mg, B, P, O and Cl. A number of these elements, for example Cu, Al and Fe, show catalytic activity in the hydrochlorination and LTC and their presence therefore may well be desired.

$Si_{mg}$ typically comprises carbon in an amount of 1 to 2500 ppmw. Generally, the carbon content is above 300 ppmw. This carbon may be present in bound form as silicon carbide (SiC) (inorganic carbon). Carbon may also be present on the surface of the $Si_{mg}$ in the form of organic compounds (for example hydraulic oils) and elementally in its allotropic forms. The carbon is introduced in particular during the production process of $Si_{mg}$ (for example via electrodes and reducing agents), in comminution processes (by grinding/crushing plants) and in classification processes (by sieving/sifter plants).

The majority of the carbon present in $Si_{mg}$ is generally in the form of SiC and appears to exhibit inert behavior in the hydrochlorination and LTC processes (Hesse K., Pätzold U.: Survey over the TCS process, Silicon for the Chemical Industry VIII 2006, 157-166). A small portion of the carbon reacts to afford methyl chlorosilanes in the abovementioned processes. Organic impurities may react to afford short-chain hydrocarbons and chlorohydrocarbons under the conditions of the hydrochlorination and LTC processes. Some of these byproducts have a similar boiling point to the chlorosilanes to be retained, in particular TCS, and can therefore be separated by distillation only with difficulty (Kohno H., Kuroko T., Itoh H., Quality requirements for silicon metal in polysilicon production, Silicon for the Chemical Industry II, 1994, 165-170).

Particularly methyldichlorosilane (MDCS) and hydrocarbons of the C5 fraction (isopentane, pent-1-ene, pent-2-ene) can be separated by distillation only at great cost. A separation process is typically carried out in a system consisting of a plurality of distillation columns. This results both in high capital costs and in high energy consumption. Disposal of the resulting chlorosilane streams in which the byproducts are enriched represents a further problem.

A process for removing MDCS based on adsorption on a solid phase is known from JP2004149351A2. Furthermore, EP 2 957 543 A1 discloses a process based on conversion of MDCS which is difficult to separate by distillation into methyltrichlorosilane (MTCS) which is easier to separate. However, these approaches include further additional and costly process steps and therefore result only in an insubstantial reduction in energy consumption and capital costs.

Rong et al. describe a process which aims to differentiate between different carbon species on or in $Si_{mg}$ (Rong et al., Analytical method to measure different forms of carbon in silicon, Silicon for the Chemical and Solar Industry XI, 2012, 145-156). To determine the carbon species the $O_2$-reactive total carbon content of the $Si_{mg}$ is analyzed with a LECO C-200 automatic combustion apparatus. Also determined with a LECO RC-612 automatic combustion apparatus is the content of free carbon which by definition is the proportion of carbon which reacts with $O_2$ at temperatures of 950° C. and 600° C. It is intimated that the TCS synthesis (hydrochlorination) proceeding from $Si_{mg}$ can result in the formation of carbon-containing byproducts. However, the largest part by far of the carbon species which contaminate the $Si_{mg}$ is inert under the reaction conditions of the hydrochlorination and thus would not lead to the formation of byproducts. A connection between the analytically captured impurities and the formation of the byproducts is not established. Also problematic are the temperature ranges chosen which resulted in overestimation of the free carbon.

SUMMARY OF THE INVENTION

The present invention has for its object to reduce the proportion of undesired byproducts in chlorosilane production and thus to reduce the costs and energy requirements for purification of chlorosilanes. This problem is solved by a process for classification of $Si_{mg}$ containing impurities of carbon and/or carbon-containing compounds comprising the steps of:
  a) determining a free carbon proportion which reacts with $O_2$ up to a temperature of 700° C. and
  b) assigning and/or providing $Si_{mg}$ in which the free carbon proportion is less than or equal to 150 ppmw for a process for producing chlorosilanes and/or assigning and/or providing $Si_{mg}$ in which the free carbon proportion is greater than 150 ppmw for a process for producing methylchlorosilanes.

DETAILED DESCRIPTION OF THE PREFERRED EMBODIMENTS

Figure 1:
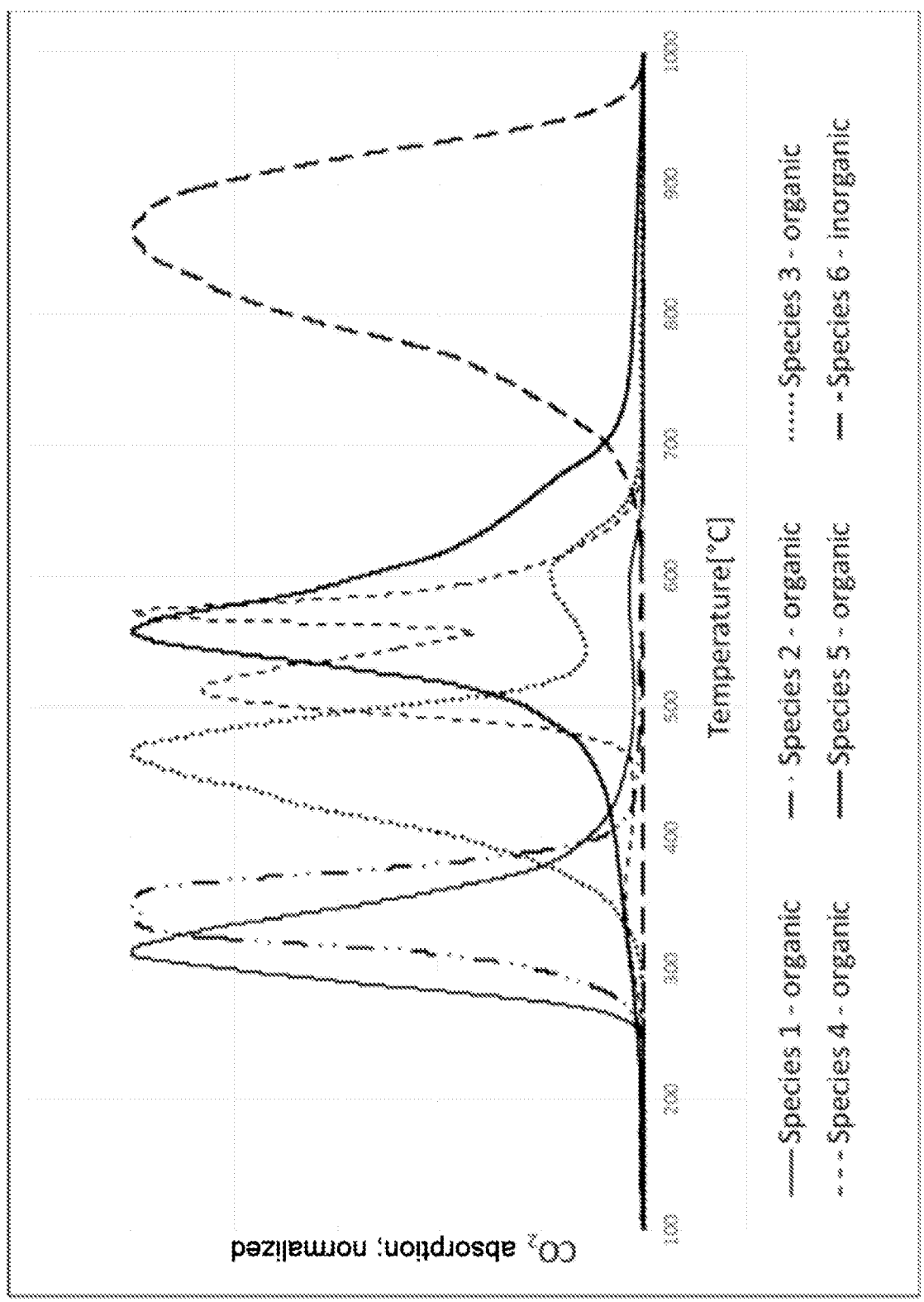
FIGS. 1-3 illustrate thermograms of various $Si_{mg}$ samples as described herein.

It is preferable when $Si_{mg}$ in which the free carbon proportion is ≤80 ppmw, more preferably ≤30 ppmw, and most preferably ≤10 ppmw, is assigned to the process for producing chlorosilanes and/or $Si_{mg}$ in which the free carbon proportion is >80 ppmw, preferably >30 ppmw, more preferably >10 ppmw, is assigned to the process for producing methylchlorosilanes.

In the context of the present invention "free carbon" is to be understood as meaning the carbon proportion of the $Si_{mg}$ to be classified which reacts with $O_2$ at up to a temperature of 700° C., preferably using a LECO RC-612 automatic combustion apparatus or its equivalent (cf. also DIN 19539). The free carbon is typically organic carbon (for example oils, fats).

By contrast, "surface carbon" is to be understood as meaning the total carbon present on the surface of the $Si_{mg}$. This comprises not only the free carbon but also the carbon which reacts with $O_2$ at above 700° C. which is mainly inorganic carbon, for example SiC.

In turn, the term "total carbon" includes not only the free carbon and the surface carbon but also the carbon present in the interior of the $Si_{mg}$ (bulk carbon).

It was found that the free carbon proportion which reacts with $O_2$ in particular in a temperature range of 100° C. to 700° C. does not exhibit inert behavior under the reaction conditions of chlorosilane production (in particular by LTC and hydrochlorination) but rather results in the formation of byproducts. These can be separated from the desired chlorosilanes, in particular TCS, only with difficulty. By contrast, the inorganic carbon which reacts with $O_2$ at above 700° C. exhibits inert behavior in the process for chlorosilane production. It has further been found that the free carbon proportion is proportional to the amounts of carbon-containing byproducts formed in the processes for producing chlorosilanes, so that using the free carbon content a qualitative grading of the $Si_{mg}$ may be effected. For example $Si_{mg}$ having a free carbon proportion of less than or equal to 10 ppmw obtains the quality grade 1 since only a small amount of byproducts is to be expected in the chlorosilane production (cf. table 4).

Alternatively or in addition to a static determination of the free carbon proportion at 700° C. according to step a) the determination may also be carried out in temperature-fractionated fashion for at least one of the temperature ranges from 360° C. to 400° C., from 480° C. to 550° C. and from 610° C. to 670° C. The free carbon proportion determined in the respective temperature range is correlated with an amount of at least one byproduct characteristic for the respective temperature range that is formed in the process for producing chlorosilanes. The $Si_{mg}$ may then be evaluated in terms of its quality according to this correlation. To illustrate the free carbon consent of the temperature ranges it is preferable to traverse a temperature gradient between 100° C. and 700° C. (temperature ramp, dynamic determination) and plot the determined amount of free carbon against temperature (thermogram).

It was recognized that from the free carbon amount determined in each of the three temperature ranges it is possible to extrapolate in each case the amount of at least one byproduct formed during the chlorosilane production. Each temperature range may be assigned at least one byproduct whose concentration increases the higher the determined free carbon proportion in the corresponding temperature range. The correlation may be performed in particular based on comparative/reference data.

It is preferable when the free carbon proportion determined in the temperature range from 360° C. to 400° C. is correlated with an amount of isopentane, the proportion determined in the temperature range from 480° C. to 550° C.

is correlated with an amount of MTCS and the proportion determined in the temperature range from 610° C. to 650° C. is correlated with an amount of MDCS.

These three byproducts are typical compounds occurring in the production of chlorosilanes which each have a similar boiling point to the desired products, in particular TCS, and can therefore be separated only at great cost.

The $Si_{mg}$ may then optionally also be assigned to different processes for producing chlorosilanes according to the correlation. This assignment may in particular be based on the preferred reaction temperatures at which for example the LTC and hydrochlorination are performed. If for example a high proportion of MDCS (corresponds to a high free carbon proportion in the temperature range from 610° C. to 650° C.) is to be expected with the classified $Si_{mg}$ it may be preferable to supply the $Si_{mg}$ to the hydrochlorination which generally proceeds at lower temperatures.

In addition to the choice of whether an $Si_{mg}$ to be processed shall be supplied to chlorosilane production at all it is thus also possible to differentiate between different processes for chlorosilane production. It is also possible to extrapolate the amounts of byproducts to be expected, thus making it possible to optimize the purification of the chlorosilanes.

It is preferable when the process for producing chlorosilanes is a hydrochlorination or an LTC.

The hydrochlorination preferably proceeds in a temperature range from 280° C. to 400° C., more preferably 320° C. to 380° C., and in particular 340° C. to 360° C. The LTC process preferably proceeds in a temperature range from 350° C. to 850° C., more preferably 400° C. to 750° C., and in particular 500° C. 700° C.

The produced chlorosilanes produced are in particular chlorosilanes of general formula $H_nSiCl_{4-n}$ and/or $H_mCl_{6-m}Si_2$ where n=1 to 4 and m=0 to 4. It is preferable when the chlorosilanes are selected from the group comprising TCS, dichlorosilane, monochlorosilane, $Si_2Cl_6$, $HSi_2Cl_5$ and mixtures thereof. It is particularly preferable when TCS is produced.

The process for producing methylchlorosilanes is preferably a Müller-Rochow synthesis which typically proceeds at a temperature of 250° C. to 350° C. and a pressure of 0.1 to 0.5 MPa. It is preferable when the produced methylchlorosilanes are selected from the group comprising trimethylchlorosilane, dimethyldichlorosilane, dimethylchlorosilane, MDCS, MTCS and mixtures thereof. Dimethyldichlorosilane is preferred in particular.

It is preferable when the $Si_{mg}$ for the process according to the invention has a particle size of 1 to 1000 μm, more preferably 50 to 500 μm, and most preferably 100 to 200 μm.

Determination of the Free Carbon Proportion of an $Si_{mg}$ Sample:

The results from the determination of the free carbon proportion make it possible to identify and thus select particularly advantageous $Si_{mg}$ starting material for the synthesis of chlorosilanes, in particular of TCS. The particular advantage of the process according to the invention is that it avoids the formation of carbon-containing byproducts and concomitantly results in a reduced load on the distillation processes arranged downstream of the chlorosilane production. Particularly advantageously the process allows even $Si_{mg}$ that is severely contaminated with inorganic carbon (which reacts with $O_2$ at temperatures of >700° C.) to be selected for chlorosilane production without any danger of increased formation of byproducts. Thus for example $Si_{mg}$ batches hitherto excluded from chlorosilane production exclusively on account of their excessively high total carbon content may nevertheless be used for chlorosilane production if the process according to the invention determines that the free carbon content is merely 150 ppmw or lower (cf. table 4). In addition, the determination of the total carbon content in the operational monitoring may be dispensed with, i.e. a second analytical instrument such as the LECO C-200 may be eschewed. It is also possible to dispense with the costly analysis of carbon-containing compounds from the $Si_{mg}$ surface by extraction followed by NMR and IR spectroscopy which has hitherto been customarily carried out.

To determine the free carbon content it is preferable to use the LECO RC-612 carbon analyzer. With the LECO RC-612 it is systemically impossible to determine total carbon and instead only surface carbon can be determined. In the LECO RC-612 in principle the pure $Si_{mg}$ sample (without additives) is heated and only the carbon disposed at the surface of the $Si_{mg}$ particles is combusted in the $O_2$ stream and the $CO_2$ formed is captured quantitatively by means of an IR measuring cell.

During the determination of the content of surface carbon (or else of the content of free carbon) the surface carbon contaminations reactive at the chosen measurement temperatures are completely oxidized to $CO_2$ in the $O_2$ stream. $O_2$ serves both as a carrier gas and as a combustion gas. The $CO_2$ concentration in the thus-obtained measurement gas is determined in standard fashion by means of the IR flow-through cells integrated into the analytical instrument. The result is calculated as the mass fraction of surface carbon (or free carbon) based on the sample mass.

The analytical instrument is typically additionally fitted with a unit for $O_2$ prepurification. This unit oxidizes any traces of hydrocarbons in the $O_2$ catalytically with copper oxide at 600° C. to afford $CO_2$ before contact with the $Si_{mg}$ sample and fully removes from the $O_2$ the resulting $CO_2$ and any water present by means of suitable absorption media (for example magnesium perchlorate and sodium hydroxide). This prepurification allows for the use of technical $O_2$ having a purity of >99.5% ($O_2$ quality 2.5). Tests with purer $O_2$ of quality 5.0 (>99.999%) generally do not give a better result.

After the prepurification, the $O_2$ is conducted into a horizontal heated quartz tube. The quartz tube forms a system open to the atmosphere. Entry of air is prevented by a first permanent purge stream of prepurified $O_2$. A second stream of prepurified $O_2$ is conducted in the opposite direction to the first stream and passes at the measurement position over the $Si_{mg}$ sample arranged in a sample boat made of quartz. Prevailing at the measurement position is the chosen measurement temperature at which the surface carbon of the $Si_{mg}$ sample is to be determined.

After leaving the quartz tube the measurement gas enriched with the oxidation products of the $Si_{mg}$ sample is conducted through a post-combustion chamber at 850° C. and is then fully oxidized to $CO_2$ at 750° C. over a copper oxide catalyst. The $CO_2$ content in the measurement gas is determined in standard fashion by IR spectroscopy in two flow-through cells having lengths of 17.78 mm (0.7 inches; high cell) and 152.4 mm (6 inches; low cell) at −2349 cm$^{-1}$. Before the measurement gas leaves the analytical instrument via a chimney it is freed of $CO_2$ and water by absorption media as also used in the $O_2$ prepurification. Calibration of the two IR cells is carried out using calcium carbonate standards for the high cell and an aqueous mannitol standard for the low cell. The calibration of the cells is carried out under measurement conditions.

The analytical limit of detection is calculated from measured results of blank value measurements from one day of measurement according to the blank value method via an SPC system (statistical process control). Deviations result in the user obtaining a warning so that measures for adhering to the defined limits may be introduced.

To avoid measurement errors, the measurement procedure is preferably performed in a laminar flow box of purity class 7 (10 000; according to ISO 14644-1). The laminar flow box may further be arranged in a clean room of purity class 8 (100 000; according to ISO 14644-1).

The LECO RC-612 carbon analyzer is capable of measuring surface carbon both at a constant measurement temperature (statistical measurement method) and with a defined temperature ramp (dynamic measurement method) between 60 and 120 K*min$^{-1}$ in the range from 100° C. to 1100° C. Statistical measurement in particular seeks to achieve quantitative determination of the total surface carbon. Dynamic measurement in particular seeks to achieve qualitative distinguishing of different carbon species on the surface of the $Si_{mg}$. The measurement conditions of the two measurement methods are summarized in table 1.

TABLE 1

| | Statistical measurement method | Dynamic measurement method |
|---|---|---|
| $O_2$ flow of purge gas [L*min$^{-1}$] | 4.0 | 4.0 |
| $O_2$ flow of reaction and carrier gas over the sample [L*min$^{-1}$] | 0.75 | 0.40 |
| Measurement time [s] | 55 | 120 |
| Sample weight [g] | 2.5 | 2.5 |
| Measurement temperature [° C.] | 1000 (C[surf.]) and 700 (C[free]) | 100-1000 (C[surf.]) and 100-700 (C[free]) |
| Temperature gradient [K*min$^{-1}$] | 0 | 120 |
| Analytical limit of detection for carbon | 20 ppbw | 80 ppbw |

The degradation behavior of carbon compounds, such as for example of hydrocarbons or of polymers, is generally dependent on factors such as the presence and concentration of an oxidant (for example oxidative degradation by $O_2$), action of heat (thermal degradation), action of light (for example photo degradation by UV light), chemical composition (structure, degree of crosslinking, saturation, crystallinity, formulation) and mixtures of fillers, polymerization catalysts, stabilizers, inhibitors and flame retardant additives. In the dynamic measurement method the temperature-dependent thermooxidative degradation of carbon compounds is utilized as a principle for distinguishing carbon species on the $Si_{mg}$ surface. Different carbon species result in characteristic thermograms. The criteria for distinguishing carbon species by thermograms are the initial temperature (commencement of thermooxidative degradation) and the curve shape (gradient, position and number of maxima). Distinguishing carbon species by substances or substance classes is typically carried out by comparisons with reference thermograms.

In a further aspect the invention provides a process for producing chlorosilanes, in particular TCS, in a fluidized bed reactor by reaction of a hydrogen chloride-containing reaction gas with a particulate contact mass containing $Si_{mg}$, wherein the $Si_{mg}$ previously passes through the described classification process.

The invention further provides a process for producing chlorosilanes, in particular TCS, in a fluidized bed reactor by reaction of a hydrogen chloride-containing reaction gas with a particulate contact mass containing $Si_{mg}$ having a total carbon content of up to 2500 ppmw, preferably up to 1500 ppmw, particularly preferably up to 750 ppmw, wherein the proportion of free carbon is not more than 150 ppmw. It is preferable when the $Si_{mg}$ for the process has a total carbon content of 400 to 2500 ppmw.

Batches of $Si_{mg}$ having such a high total carbon content have hitherto typically not been supplied to chlorosilane production. However, the selection process according to the invention makes it possible for such batches to be used for chlorosilane production. This makes it possible in particular to reduce costs since the price of $Si_{mg}$ increases with increasing purity.

The processes are preferably a hydrochlorination or an LTC.

The described processes are preferably incorporated in an integrated system for producing polycrystalline silicon. The integrated system preferably comprises the following processes:

classification of $Si_{mg}$ and assignment for chlorosilane production by the process according to the invention,
  production of chlorosilanes, in particular TCS, by hydrochlorination or LTC,
  purification of the produced chlorosilanes to afford semiconductor quality TCS chlorosilanes,
  deposition of polycrystalline silicon, preferably by the Siemens process or the granulate process.

The invention further provides for the use of $Si_{mg}$ having a total carbon content of up to 2500 ppmw, preferably up to 1500 ppmw, more preferably up to 750 ppmw, for producing chlorosilanes, in particular TCS, wherein the proportion of free carbon is not more than 150 ppmw.

It is preferable to employ $Si_{mg}$ having a total carbon content of 400 to 2500 ppmw for chlorosilane production.

EXAMPLES

FIG. 1 shows by way of example such a reference thermogram, wherein each curve corresponds to an sample contaminated with a $Si_{mg}$ known organic polymeric pure substance (species 1 to 5—organic) or typical inorganic carbon species such as carbonates, carbides and allotropic forms of carbon (species 6—inorganic). While thermooxidative degradation of the organic carbon species takes place in the temperature range from about 250° C. to 750° C. the initial temperature of thermooxidative degradation of the inorganic carbon compounds is about 650° C. The $CO_2$ absorption measured in the IR cells is directly proportional to $CO_2$ concentration and was normalized to a value of one (i.e. the highest measured value is normalized to one in each case).

Figure 2:
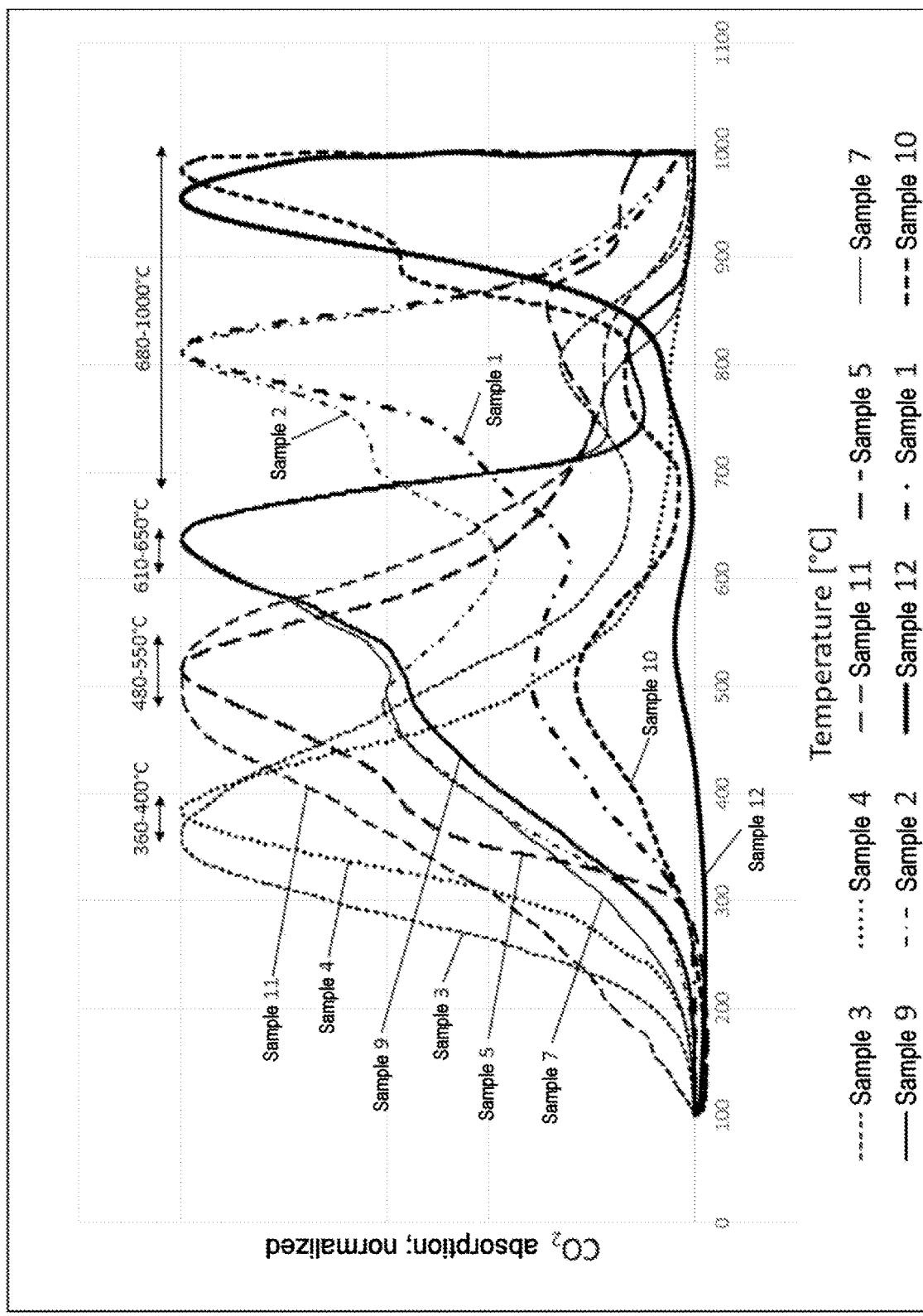

FIG. 2 shows thermograms of ten samples from ten different batches of $Si_{mg}$ (samples 1 to 5, 7, 9, 10 to 12) in a measurement range of 100° C. to 1000° C. The thermograms show both monomodal (for example sample 4) and multimodal (for example samples 9, 10) curve shapes. It is deducible from a monomodal curve shape that the particular sample is predominantly contaminated with only one carbon-containing substance or with different substances having very similar oxidation properties (for example identical substance classes). However, the samples predominantly show multimodal thermograms from which it may be deduced that these samples are contaminated with a plurality of carbon-containing substances which differ in their oxidation properties. The integral area of a thermogram is directly proportional to the content of carbon. Consequently, the integral area below a peak is directly proportional to the proportion of a particular carbon-containing substance or substance class.

It has been found that in the temperature range of thermooxidative degradation of organic carbon species there are three characteristic temperature ranges in which the measured amount of free carbon in each case correlates with at least one byproduct in chlorosilane production:

Temperature range 1: 360° C.-400° C.
Temperature range 2: 480° C.-550° C.
Temperature range 3: 610° C.-650° C.

In the thermograms of the samples inorganic carbon species show similar groupings above a temperature of >680° C. (temperature range 4: 680° C.-1000° C.).

In order to determine whether the carbon-containing impurities corresponding to the temperature ranges 1 to 3 can be assigned to the formation of certain byproducts in processes for producing chlorosilanes the $Si_{mg}$ batches investigated were reacted to produce TCS in the hydrochlorination and the LTC. The gas leaving the test reactor was fully condensed and analyzed quantitatively and qualitatively by gas chromatography. Carbon compounds (byproducts) such as for example isopentane, MDCS and MTCS were detected in different concentrations. Analysis of the data surprisingly revealed a correlation between the byproducts formed (in type and concentration) and the signals appearing in the temperature ranges 1 to 3.

1. The content of isopentane in the condensate after TCS production is directly proportional to the measured proportion of carbon-containing impurity (area below the signal) in temperature range 1.
2. The content of MTCS in the condensate after TCS production is directly proportional to the measured proportion of carbon-containing impurity (area below the signal) in temperature range 2.
3. The content of MDCS in the condensate after TCS production is directly proportional to the measured proportion of carbon-containing impurity (area below the signal) in temperature range 3.
4. The signals obtained in the dynamic surface carbon measurement at temperatures >680° C. (temperature range 4) show no correlations whatsoever in respect of the formation of a byproduct during TCS production. These carbon species are inert in the prevailing reaction conditions of hydrochlorination and LTC.

This is shown by way of example for the $Si_{mg}$ samples 4, 6, 8 and 12.

Figure 3:
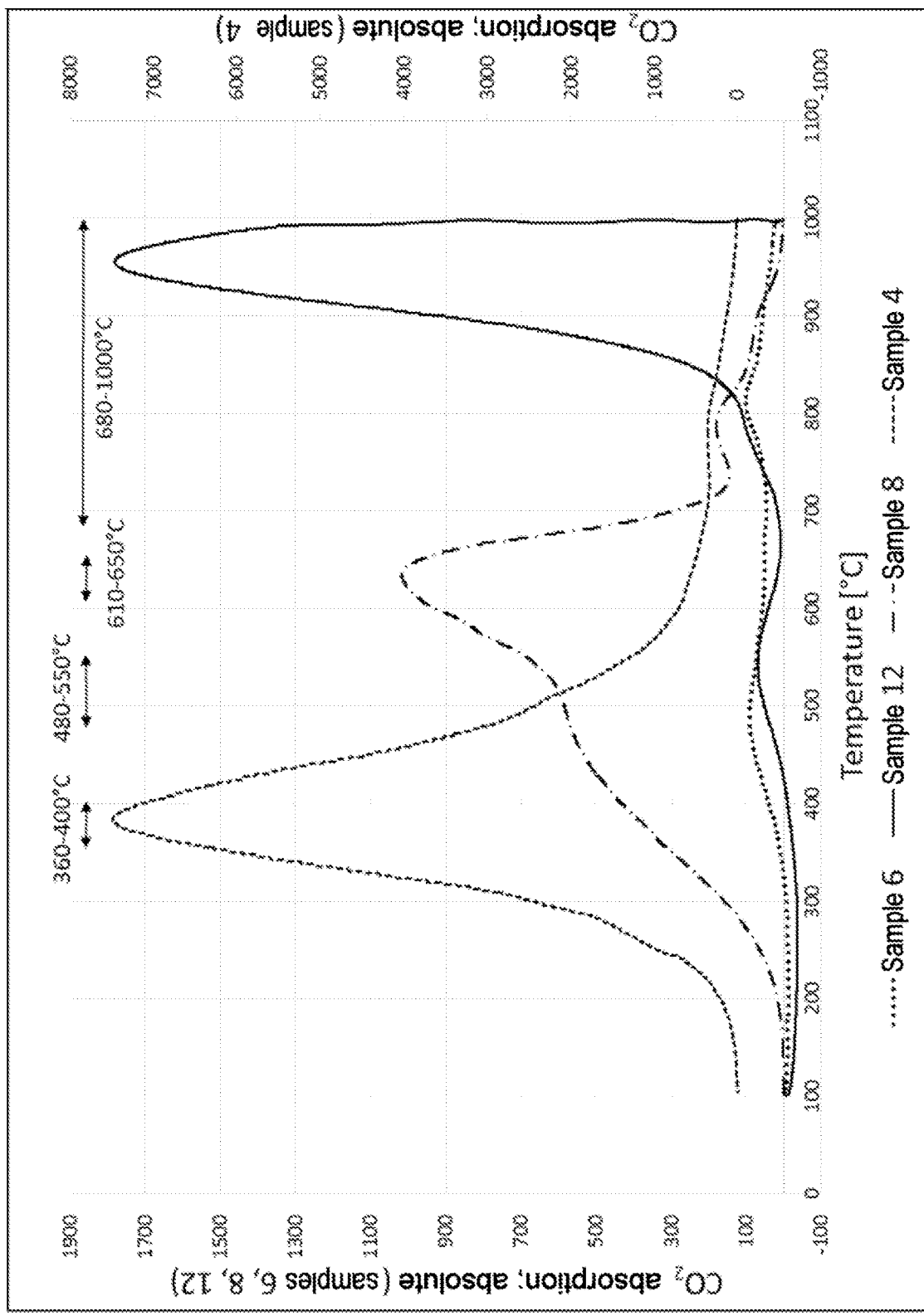

The $Si_{mg}$ samples 4, 6, 8 and 12 were subjected to the abovementioned measurement procedures to determine surface carbon (temperature 100-1000° C.) and free carbon (temperature 100-700° C.). FIG. 3 shows the thermograms obtained. $CO_2$ absorption is reported as an absolute value (actual measured value from IR measuring cells).

The $Si_{mg}$ batches associated with the samples 4, 6, 8 and 12 were converted in the hydrochlorination and the amounts of isopentane, MDCS and MTCS in the product condensate were determined. The hydrochlorination was carried out in a fluidized bed reactor for each of the four batches (cf. U.S. Pat. No. 4,092,446, FIG. 12). A bed of $Si_{mg}$ is purged with nitrogen until a fluidized bed is formed. The quotient of fluidized bed height and reactor diameter has a value of about 5. The temperature of the fluidized bed is adjusted to about 340° C. and is kept approximately constant by cooling. Then hydrogen chloride and $Si_{mg}$ are added/metered in subsequently such that the height of the fluidized bed remains constant over the test duration and a constant mole ratio of the reactants of 3:1 ($HCl:Si_{mg}$) is established. The pressure in the reactor is typically 1 bar ($10^5$ Pa, positive pressure). After a run time of 48 h a liquid sample (condensate) is withdrawn. The condensable proportions of the product gas stream are condensed via a cold trap at −40° C. and the liquid obtained is analyzed by gas chromatography to determine the amount of carbon-containing byproducts. Detection is effected via a thermal conductivity detector. The analytical results of two samples withdrawn after 48 h are in each case used to form averages. Analysis of the carbon-containing byproducts in the LTC is carried out analogously.

Evaluation of the four batches (samples 4, 6, 8, 12) in terms of their quality for the production of chlorosilanes was carried out based on the results of a multiplicity of tests with various $Si_{mg}$ batches and an estimate of the costs generated by their use for distillative purification of the corresponding product mixture for producing high-purity TCS.

The results obtained are summarized in tables 2 and 3.

TABLE 2

|  | c(isopentane) [ppbw] | c(MTCS) [ppbw] | c(MDCS) [ppbw] | IR absorpt. low cell; temp. range 1 | IR absorpt. low cell; temp. range 2 | IR absorpt. low cell; temp. range 3 |
|---|---|---|---|---|---|---|
| Sample 6 | 216 | 3107 | 2779 | 26.5 | 84.3 | 51.1 |
| Sample 12 | 174 | 5023 | 5018 | 0 | 58.7 | 19.0 |
| Sample 8 | 4013 | 16231 | 14.923 | 380.2 | 611.7 | 1001.6 |
| Sample 4 | 57.743 | 22.386 | 12.139 | 6263.0 | 2040.3 | 579.0 |

TABLE 3

|  | c(surface C) [ppmw] | quality (isopentane) | Quality (MTCS) | quality (MDCS) | quality average |
|---|---|---|---|---|---|
| Sample 6 | 7 | 1 | 1 | 1 | 1.0 |
| Sample 12 | 68 | 1 | 1 | 1 | 1.0 |
| Sample 8 | 62 | 3 | 3 | 3 | 3.0 |
| Sample 4 | 423 | 6 | 5 | 4 | 5.0 |

A surface carbon content (c(surface C)) of 68 ppmw (sample 12) would actually point to only average properties in terms of the formation of carbon-containing byproducts. However, since the surface carbon in sample 12 is attributable to the inorganic range above about 700° C. according to the thermogram in FIG. 3 the corresponding $Si_{mg}$ nevertheless results only in a very low formation of carbon-containing byproducts in TCS production. This confirms that under the reaction conditions of TCS synthesis (hydrochlorination and LTC) inorganic carbon compounds are not converted into disruptive byproducts and may be regarded as inert.

Sample 8 exhibits in the thermogram (FIG. 3) strong signals in the temperature ranges 2 and 3 which correlate with the formation of MTCS and MDCS. The surface carbon is thus mainly free carbon. Sample 8 with its amount of surface carbon of 62 ppmw is still in an acceptable range for TCS synthesis (quality grade 3).

Sample 4 exhibits a very strong signal in the temperature range 1 that correlates with the formation of isopentane and this is confirmed by GC analysis at the end of TCS production (c(isopentane)=57,743 ppbw). An amount of surface carbon of 423 ppmw results overall. Since this is mainly free carbon the $Si_{mg}$ batch from which sample 4 was taken results in an inadequate overall result (quality grade 5). Such batches are therefore assigned to the production of methylchlorosilanes. It should be noted that for sample 4 in FIG. 3 the secondary axis (right-hand side) is decisive. Samples 4 and 8 exhibit only very low signals above 700° C. as a result of which the carbon contents in this range are negligible. Evaluation according to table 4 (measurement range 100° C. to 700° C.) is therefore possible.

Sample 6 exhibits a very low surface carbon content of 7 ppmw. In the range between 100° C. and 700° C. the thermogram of sample 6 is similar in profile to that of sample 12. Only very low amounts of isopentane, MTCS and MDCS are to be expected and this is confirmed by the GC analysis at the end of TCS production.

Since ultimately only the content of free carbon (reaction with $O_2$ up to 700° C.) is decisive for the quality of the $Si_{mg}$ in terms of the formation of undesired byproducts in the production of chlorosilanes, and thus for its usability, it is also possible in normal operation to carry out measurements only at 700° C. (static) or in a temperature range from 100° C. to 700° C. (dynamic). The free carbon determined at these temperatures may be used to perform the classification into the quality grades (cf. table 4) wherein $Si_{mg}$ batches of quality grades 5 and 6 are generally assigned to a process for producing methylchlorosilanes.

TABLE 4

| Surface carbon concentration [ppmw] up to 700° C. | Quality grade |
|---|---|
| <10 | 1 |
| >10-30 | 2 |
| >30-80 | 3 |
| >80-150 | 4 |
| >150-300 | 5 |
| >300 | 6 |

Figure 4:
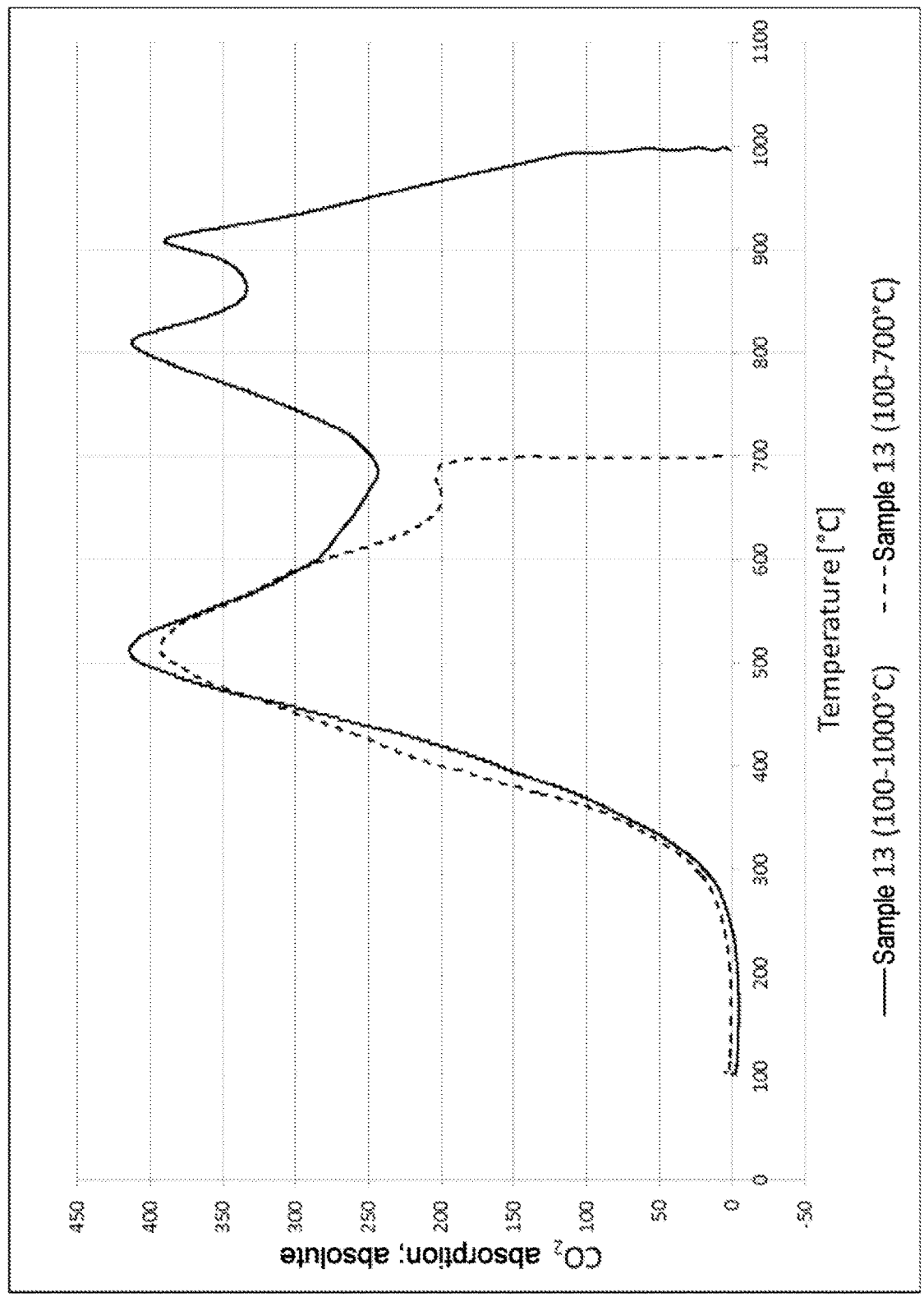
FIG. 4 illustrates a comparison between dynamic measurement of two $Si_{mg}$ samples at 1000° C. and 700° C.

Dynamic measurement is advisable when evaluation in respect of the approximate quantity ratio of different byproducts is to be carried out. A comparative representation between a dynamic measurement of a sample of $Si_{mg}$ (sample 13) up to 1000° C. and up to 700° C. is shown in FIG. 4.

The invention claimed is:

1. A process for improving chlorosilane production from metallurgical grade silicon, comprising:
   a) analyzing a plurality of portions of metallurgical silicon containing impurities of carbon and/or carbon-containing compounds to determine a free carbon proportion in the metallurgical grade silicon which reacts with oxygen at a temperature of 700° C. or below using an automatic combustion process,
   b) classifying portions of metallurgical grade silicon in which the free carbon proportion is present in a proportion ≤150 ppmw as low free carbon metallurgical grade silicon and classifying portions of metallurgical grade silicon having a free carbon content higher than that of the low free carbon metallurgical grade silicon as high free carbon metallurgical grade silicon; and producing trichlorosilane and methylchlorosilanes by the steps of:
   c) producing trichlorosilane from low free carbon metallurgical grade silicon portions by a hydrochlorination process or a low temperature conversion process, and
   d) producing methylchlorosilanes from high free carbon metallurgical grade silicon portions by a Müller-Rochow process.

2. The process of claim 1, wherein low free carbon metallurgical grade silicon portions in which the free carbon proportion is ≤80 ppmw are directed to the hydrochlorination process and/or to the low temperature conversion process for producing chlorosilanes.

3. The process of claim 1, wherein high free carbon metallurgical grade silicon portions in which the free carbon proportion is >80 ppmw, are directed to the Müller-Rochow process for producing methylchlorosilanes.

4. The process of claim 1, wherein low free carbon metallurgical grade silicon portions in which the free carbon proportion is ≤30 ppmw are directed to the hydrochlorination process and/or to the low temperature conversion process for producing chlorosilanes.

5. The process of claim 1, wherein high free carbon metallurgical grade silicon in which the free carbon proportion is >30 ppmw, are directed to the Müller-Rochow process for producing methylchlorosilanes.

6. The process of claim 1, wherein low free carbon metallurgical grade silicon in which the free carbon proportion is ≤10 ppmw is directed to the hydrochlorination process and/or to the low temperature conversion process for producing chlorosilanes, and high free carbon metallurgical grade silicon in which the free carbon proportion is >10 ppmw is directed to the Müller-Rochow process for producing methylchlorosilanes.

7. The process of claim 1, wherein determination of the free carbon proportion is carried out in a temperature-fractionated fashion for at least one of the temperature ranges from 360° C. to 400° C., from 480° C. to 550° C. and from 610° C. to 670° C., wherein the free carbon proportion determined in the temperature range from 360° C. to 400° C. is correlated with an amount of isopentane, the free carbon proportion determined in the temperature range from 480° C. to 550° C. is correlated with an amount of methyltrichlorosilane, and the free carbon proportion determined in the temperature range from 610° C. to 650° C. is correlated with an amount of methyldichlorosilane and the metallurgical grade silicon is assigned a quality rating according to the above correlations.

8. The process of claim 7, wherein the metallurgical grade silicon is directed to different processes for producing chlorosilanes according to the correlation.

9. The process of claim 1, wherein the metallurgical silicon has a particle size of 1 to 1000 μm.

10. The process of claim 1, wherein the metallurgical silicon has a particle size of 50 to 500 μm.

11. The process of claim 1, wherein the metallurgical silicon has a particle size of 100 to 200 μm.

12. A process for producing chlorosilanes employing metallurgical grade silicon by a chlorosilane process which is a hydrochlorination process or a low temperature conversion process, comprising the steps of:
   a) analyzing the metallurgical grade silicon portions to determine a free carbon proportion which reacts with oxygen at a temperature of 700° C. or below, b) directing low free carbon metallurgical silicon portions in which the free carbon proportion is less than or equal to a target value which is ≤150 ppmw, to the chlorosilane process, and c) reacting a particulate contact mass containing the metallurgical grade silicon from step b) with a hydrogen chloride-containing reaction gas in the hydrochlorination process and/or with tetrachlorosilane and hydrogen in the low temperature conversion process, and d) recovering chlorosilanes produced in the respective processes of step c), e) directing metallurgical grade silicon having a higher free carbon content than the low free carbon metallurgical grade silicon to a Müller-Rochow process for producing methylchlorosilanes, and f) recovering methylchlorosilanes from the process of step e).

13. The process of claim 12, wherein both the hydrochlorination and low temperature conversion processes are practiced.

14. The process of claim 12, wherein the metallurgical grade silicon has a total carbon content of up to 2500 ppmw.

15. The process of claim 12, wherein the metallurgical silicon has a total carbon content of 400 to 2500 ppmw.

16. The process of claim 12, wherein chlorosilanes of the formula $H_nSiCl_{4-n}$ and/or $H_mCl_{6-m}Si_2$ where n=1-4 and m=0-4 are produced.

17. The process of claim 13, wherein the chlorosilanes are selected from the group comprising of trichlorosilane, dichlorosilane, monochlorosilane, $Si_2Cl_6$, $HSi_2Cl_5$, and mixtures thereof.

18. A process for the production of chlorosilanes, comprising:

a) providing a chlorosilane production plant having a)i) at least one trichlorosilane production process selected from the group consisting of a hydrochlorination process and a low temperature conversion process and a)ii) at least one Müller-Rochow methylchlorosilane production process;

b) supplying portions of metallurgical grade silicon having varying amounts of free carbon and total carbon as impurities, to the production plant;

c) analyzing the free carbon content of the metallurgical grade silicon and classifying the portions of metallurgical grade silicon into low free carbon metallurgical grade silicon portions and high free carbon metallurgical grade silicon portions, a cut-off between a designation as low free carbon and a designation as high free carbon being a value of free carbon content which is ≤150 ppmw based on the weight of the metallurgical grade silicon portion;

d) producing trichlorosilane from the low free carbon metallurgical grade silicon portions from step c) by a process of a)i); and e) producing methylchlorosilanes from the high free carbon metallurgical grade silicon portions from step c) by the process a)ii).

19. The process of claim 18, wherein low free carbon metallurgical grade silicon is defined as metallurgical grade silicon having a free carbon content of ≤80 ppmw, and high free carbon silicon is defined as metallurgical grade silicon having a free carbon content of >80 ppmw.

20. The process of claim 18, wherein low free carbon metallurgical grade silicon is defined as metallurgical grade silicon having a free carbon content of ≤30 ppmw, and high free carbon silicon is defined as metallurgical grade silicon having a free carbon content of >30 ppmw.

* * * * *